US011517904B2

(12) United States Patent
Jia et al.

(10) Patent No.: US 11,517,904 B2
(45) Date of Patent: Dec. 6, 2022

(54) DIGITAL MICROFLUIDICS FOR POLYMERASE CHAIN REACTION

(71) Applicant: University of Macau, Macau (CN)

(72) Inventors: Yanwei Jia, Macau (CN); Liang Wan, Macau (CN); Cheng Dong, Macau (CN); Haoran Li, Macau (CN); Tianlan Chen, Macau (CN); Pui-In Mak, Macau (CN); Rui Paulo da Silva Martins, Macau (CN)

(73) Assignee: University of Macau, Macau (CN)

( * ) Notice: Subject to any disclaimer, the term of this patent is extended or adjusted under 35 U.S.C. 154(b) by 610 days.

(21) Appl. No.: 16/416,337

(22) Filed: May 20, 2019

(65) Prior Publication Data

US 2019/0358636 A1  Nov. 28, 2019

Related U.S. Application Data

(60) Provisional application No. 62/677,071, filed on May 28, 2018.

(51) Int. Cl.
| | |
|---|---|
| *C12Q 1/68* | (2018.01) |
| *B01L 7/00* | (2006.01) |
| *C12Q 1/686* | (2018.01) |
| *B01L 3/00* | (2006.01) |
| *G01N 27/447* | (2006.01) |

(52) U.S. Cl.
CPC ............... *B01L 7/52* (2013.01); *B01L 3/5027* (2013.01); *B01L 7/525* (2013.01); *C12Q 1/686* (2013.01); *B01L 2300/0645* (2013.01); *B01L 2300/0883* (2013.01); *B01L 2300/165* (2013.01); *B01L 2300/168* (2013.01); *B01L 2300/1811* (2013.01); *G01N 27/44747* (2013.01)

(58) Field of Classification Search
None
See application file for complete search history.

(56) References Cited

PUBLICATIONS

Chang et al. (Biomed Microdevices, 2006, 8:215-225) (Year: 2006).*
Zhang et al. (Proceedings of IMECE: 2003 ASME International Mechanical Engineering Congress and RD&D Expo, Nov. 15-21, 2003, p. 1-5) (Year: 2003).*
Norian, Stephen H (2014, Dissertation, Integrated CMOS Polymerase Chain Reaction Lab-on-Chip, p. 1-97) (Year: 2014).*

(Continued)

*Primary Examiner* — Stephanie K Mummert
(74) *Attorney, Agent, or Firm* — Spruson & Ferguson (Hong Kong) Limited

(57) ABSTRACT

Provided is a digital microfluidic device for quick polymerase chain reaction. The digital microfluidic device includes an enclosed chamber for holding droplets comprising PCR mixtures. The chamber has an upper layer and a lower layer, which provide a top heater and a bottom heater contained in a thermal electrode respectively to form dual heaters. The lower layer further has an array of electrodes and a dielectric layer, e.g. Norland Optical adhesive 61, coating thereon. Such arrangement of the digital microfluidic device allows quick and homogeneous heating of droplets to lower the heating voltage, shorten the reaction time, and prevent the dielectric layer from breakdown during the thermal cycle.

16 Claims, 10 Drawing Sheets
Specification includes a Sequence Listing.

(56) References Cited

PUBLICATIONS

Farrar, J. S. & Wittwer, C. T. Extreme PCR: efficient and specific DNA amplification in 15-60 seconds. Clin Chem 61, 145-153, doi:10.1373/clinchem.2014.228304 (2015).

Wheeler, E. K. et al. Under-three minute PCR: probing the limits of fast amplification. Analyst 136, 3707-3712, doi:10.1039/c1an15365j (2011).

Maltezos, G. et al. Exploring the limits of ultrafast polymerase chain reaction using liquid for thermal heat exchange: A proof of principle. Appl Phys Lett 97, 264101, doi:10.1063/1.3530452 (2010).

Roche, P. J. R. et al. Real time plasmonic qPCR: how fast is ultra-fast? 30 cycles in 54 seconds. Analyst 142, 1746-1755, doi:10.1039/c7an00304h (2017).

Kim, H., Dixit, S., Green, C. J. & Faris, G. W. Nanodroplet real-time PCR system with laser assisted heating. Opt Express 17, 218-227 (2009).

Choi, K., Ng, A. H., Fobel, R. & Wheeler, A. R. Digital microfluidics. Annu Rev Anal Chem (Palo Alto Calif) 5, 413-440, doi:10.1146/annurev-anchem-062011-143028 (2012).

Chang, Y. H., Lee, G. B., Huang, F. C., Chen, Y. Y. & Lin, J. L. Integrated polymerase chain reaction chips utilizing digital microfluidics. Biomed Microdevices 8, 215 225, doi:10.1007/s10544-006-8171-y (2006).

Hua, Z. et al. Multiplexed real-time polymerase chain reaction on a digital microfluidic platform. Anal Chem 82, 2310-2316, doi:10.1021/ac902510u (2010).

Sista, R. et al. Development of a digital microfluidic platform for point of care testing. Lab on a chip 8, 2091-2104, doi:10.1039/B814922D (2008).

Rival, A. et al. An EWOD-based microfluidic chip for single-cell isolation, mRNA purification and subsequent multiplex qPCR. Lab on a chip 14, 3739-3749, doi:10.1039/c4lc00592a (2014).

Coelho, B. et al. Digital Microfluidics for Nucleic Acid Amplification. Sensors (Basel) 17, doi:10.3390/s17071495 (2017).

Chen, T. et al. Sub-7-second genotyping of single-nucleotide polymorphism by high-resolution melting curve analysis on a thermal digital microfluidic device. Lab on a chip 16, 743-752, doi:10.1039/c5lc01533b (2016).

Sanchez, J. A., Pierce, K. E., Rice, J. E. & Wangh, L. J. Linear-after-the-exponential (LATE)-PCR: an advanced method of asymmetric PCR and its uses in quantitative real-time analysis. Proceedings of the National Academy of Sciences of the United States of America 101, 1933-1938, doi:10.1073/pnas.0305476101 (2004).

\* cited by examiner

DIGITAL MICROFLUIDICS FOR POLYMERASE CHAIN REACTION

CROSS-REFERENCE TO RELATED APPLICATIONS

The present application claims priority to and the benefit of U.S. Provisional Patent Application Ser. No. 62/677,071, which was filed on May 28, 2018, and is hereby incorporated by reference in its entity.

FIELD OF THE INVENTION

The present disclosure generally relates to a digital microfluidic system and methods for making and using the same, and in particular, to a digital microfluidic system and methods useful for, e.g., quick polymerase chain reaction.

BACKGROUND OF THE INVENTION

Polymerase chain reaction (PCR) is the kernel of modern molecular biology and diagnostics. This temperature-dependent technique amplifies DNA in an exponential way by cycles of heating and cooling. A typical PCR often takes 1-2 hours in a bulky thermal cycler. In clinical point-of-care diagnostics, especially for infectious diseases, both reaction time and specificity of the reaction are vital to clinical decisions. Many quick PCR methods have been developed, exploiting the miniaturization feature of microfluidics or capillary reactors. However, these methods still require large accessories to support the thermal cycling process. Other fast PCR setups using laser or plasmonic techniques are costly because they need expensive light instrument for the light source.

Digital microfluidics (DMF) is an emerging technology to manipulate individual microliter-sized to nanoliter-sized droplets on an array of electrodes by electro-wetting force. Its features of electric driving and miniature footprint render it a promising technology for point-of-care diagnostics.

However, the existing DMF systems for PCR take longer than 10 min.

Therefore, there is a need for developing a cost effective and robust DMF system for conducting quick PCR in less than 10 min.

SUMMARY OF THE INVENTION

Provided herein is a digital microfluidic device that enables, e.g. quick PCR. Other applications that require heating and cooling cycles are also within the contemplation of the present disclosure.

The digital microfluidic device of the present disclosure is capable of conducting quick PCR and the PCR thereof can successfully amplify detectable DNA products as early as 60 cycles (342 s), less than 6 minutes. Moreover, the configuration of the digital microfluidic device of the present disclosure ensures a robust system for thermal cycles, without the breakdown of any of the materials used for the device, such as dielectric layers, during the process of repeatedly heating and cooling.

In certain embodiments, the present disclosure relates to a digital microfluidic device 100 for conducting quick polymerase chain reaction in at least one droplet 600 generated from a loading fluid, the device 100 comprising an upper layer 200, a lower layer 300, a lateral wall 400 positioned between the upper layer 200 and the lower layer 300 to form a chamber, an inlet for receiving the loading fluid and providing the loading fluid to the chamber, and an outlet for releasing trapped air and extra loading fluid during a loading process, wherein: the lower layer 300 comprises: a first substrate 303; an array of electrodes comprising at least one thermal electrode 307 formed on an inner side of the first substrate 303, an individual thermal electrode comprising a heater electrode 305 and a sensor electrode 306; at least one first coating 302 covering each electrode of the array of electrodes such that all electrodes of the array of electrodes are electrically insulated from one another; and a first hydrophobic layer 301 formed on the at least one first coating 302 to provide a first hydrophobic working surface 301-1.

In certain embodiments, the upper layer 200 comprises: a second substrate 202, at least one top heater 204 formed by at least one second coating 201 covering an outer side of the second substrate 202, and a second hydrophobic layer 203 being formed on an inner side of the second substrate 202 to provide a second hydrophobic working surface 203-1.

In certain embodiments, the at least one second coating 201 is an indium tin oxide coating.

In certain embodiments, the at least one first coating 302 is an ultraviolet curable resin.

In certain embodiments, the at least one first coating 302 is a dielectric layer.

In certain embodiments, an individual thermal electrode 307 is positioned right below a corresponding top heater 204 to create a space in the chamber with the space between the individual thermal electrode 307 and the corresponding top heater 204 capable of contacting a corresponding droplet 600 located between the second hydrophobic working surface 203-1 and the first hydrophobic working surface 301-1 such that the corresponding droplet receives heat from both the upper and lower layers.

In certain embodiments, the heater electrode 305 is serpentine-shaped having an inner ring (308) and an outer ring 309.

In certain embodiments, the inner ring 308 is wider than the outer ring 309.

In certain embodiments, the inner ring 308 has a width of about 300 μm to about 400 μm, and the outer ring 309 has a width of about 200 μm to about 300 μm.

In certain embodiments, the inner ring 308 has a width of about 349 μm, and the outer ring 309 has a width of about 279 μm.

In certain embodiments, the at least one sensor electrode 306 is fork-shaped being positioned between the inner ring 308 and the outer ring 309.

In certain embodiments, the at least one heater electrode 305 and the at least one sensor electrode 306 have a distance of larger than about 100 μm.

In certain embodiments, the at least one heater electrode 305 and the at least one top heater 204 can be connected to an adjustable direct current (DC) power supply to form a first mode for providing heat to the at least one droplet 600.

In certain embodiments, the at least one heater electrode 305 can be connected to an alternating current (AC) power supply to form a second mode for transporting the at least one droplet 600 from the inlet to the at least one thermal electrode 307.

In certain embodiments, the at least one sensor electrode 306 can be connected to a direct current (DC) power supply and a voltage indicator or voltage meter to form a third mode for recording temperature of the at least one droplet 600.

In certain embodiments, the present disclosure also relates to a method for conducting quick polymerase chain reaction, comprising steps of: a) providing a digital microfluidic device 100; b) transporting at least one droplet 600 generated from a loading fluid to the at least one thermal electrode 307 of the digital microfluidic device 100; c) repeatedly heating the at least one droplet 600 for a first length of time and cooling the at least one droplet 600 for a second length of time followed by heating the at least one droplet 600 for a third length of time and cooling the at least one droplet 600 for a fourth length of time; and d) imaging the at least one droplet 600.

In certain embodiments, the method further comprises between the step a) and the step b) a step e): calibrating the at least one sensor electrode 306 to obtain a linear relationship between temperature sensed by the at least one sensor electrode 306 and voltage measured by a voltage indicator connected to the at least one sensor electrode 306.

In certain embodiments, the loading fluid comprises at least one primer, at least one DNA indicator, and at least one target DNA sequence.

In certain embodiments, the first length of time is time for increasing temperature from about 50° C. to about 95° C., and the second length of time is time for reducing temperature from about 95° C. to about 50° C.

In certain embodiments, the third length of time is obtained by reducing the first length time by 0.1-0.5 seconds, and the fourth length of time is obtained by increasing the second length of time by 0.1-0.5 seconds.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Other aspects and advantages of the invention will be apparent to those skilled in the art from a review of the ensuing description.

BRIEF DESCRIPTION OF THE DRAWINGS

The above and other objects and features of the present disclosure will become apparent from the following description of the various embodiments described herein, when taken in conjunction with the accompanying drawings, in which.

DETAILED DESCRIPTION OF THE INVENTION

For the purposes of the present disclosure, PCR reaction mixtures are described in connection with the microfluidic system and the methods using thereof described herein only as exemplary embodiments. It should be appreciated that the uses of the system and methods are not limited to PCR reaction mixtures, but also other samples that require heating and cooling cycles.

Additionally, to assist in the description of the structural configuration, words such as length, width, height, depth, upper, lower, top, bottom, transverse, longitudinal, horizontal and the like are used. Unless their contextual usage indicates otherwise, these words are to be understood herein as having no structural, functional or operational significance and as merely reflecting the arbitrarily chosen orientation.

The term "microfluidic" as used herein is to be understood, without any restriction thereto, to refer to structures or devices through which fluid, such as liquids and gases, is capable of being passed or directed, wherein one or more of the dimensions is less than about 500 µm.

As used herein the term "and/or" includes any and all combinations of one or more of the associated listed items.

The term "element" as used herein is intended to include meanings of other like-terms such as "component" and so forth.

As used herein, the term "prevent" or "preventing" refers to any method to partially or completely preclude, avert, obviate, forestall, stop, hinder or delay the consequence or phenomenon following the term "prevent" or "preventing" from happening. The term "prevent" or "preventing" does not mean that the method is necessarily absolute, but rather effective for providing some degree of prevention or amelioration of consequence or phenomenon following the term "prevent" or "preventing".

Structural Configuration of the Microfluidic Chip

Figure 1:
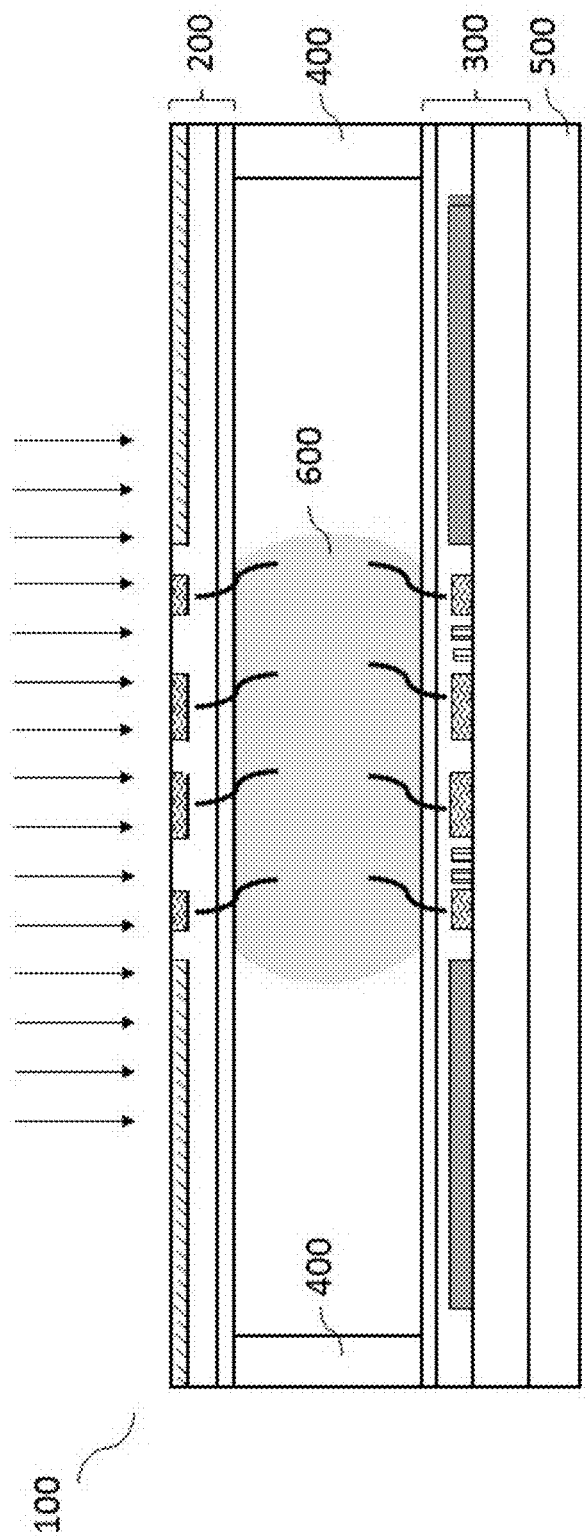
FIG. 1 illustrates a cross-sectional view of a digital microfluidic device according to certain embodiments of the present disclosure.

FIG. 1 illustrates a cross-sectional view of a digital microfluidic device 100 according to certain embodiment of the present disclosure. The digital microfluidic device 100 comprises an upper layer 200, a lower layer 300, and a lateral wall 400 positioned between the upper layer 200 and the lower layer 300 to form a chamber. In certain embodiments, the microfluidic device 100 further comprises an inlet and an outlet passing through the upper layer 200. The inlet can receive a loading fluid and provide the loading fluid to the chamber for e.g. polymerase chain reaction. The outlet can release the trapped air and extra loading fluid during the loading process. In certain embodiments, the digital microfluidic device 100 further comprises a heat sink 500.

In certain embodiments, the inlet is circular in shape and has a diameter of about 0.5 mm to about 2.5 mm, about 0.6 mm to about 2.4 mm, about 0.7 mm to about 2.3 mm, about 0.8 mm to about 2.2 mm, about 0.9 mm to about 2.1 mm, about 1.0 mm to about 2.0 mm, about 1.1 mm to about 1.9 mm, about 1.2 mm to about 1.8 mm, about 1.3 mm to about 1.7 mm, about 1.4 mm to about 1.6 mm, or about 1.5 mm. In certain embodiments, the inlet has a diameter of about 1.2 mm. The inlet can be formed by drilling the upper layer 200 using a laser cutter.

The inner side of the upper layer 200 and the inner side of the lower layer 300 can be coated with a second hydrophobic layer 203 and a first hydrophobic layer 301 respectively. The first and second hydrophobic layers provide a second hydrophobic working surface 203-1 and a first hydrophobic working surface 301-1 facing each other to facilitate the formation and/or transportation of droplets generated from a loading fluid.

In certain embodiments, the lateral wall 400 has a height of about 100 µm to about 300 µm, about 110 µm to about 290 µm, about 120 µm to about 280 µm, about 130 µm to about 270 µm, about 140 µm to about 260 µm, about 150 µm to about 250 µm, about 160 µm to about 240 µm, about 170 µm to about 230 µm, about 180 µm to about 220 µm, about 190 µm to about 210 µm, or about 200 µm. In certain embodiments, the lateral wall 400 has a height of about 200 µm. In certain embodiments, the lateral wall 400 is oil-proof double adhesive and can be sealed with UV glue.

In certain embodiments, the materials for the first hydrophobic layer and the second hydrophobic layer are the same. In certain embodiments, the materials for the first hydrophobic layer and the second hydrophobic layer are different. In certain embodiments, the thickness of the first hydrophobic layer and the thickness of the second hydrophobic layer are the same. In certain embodiments, the thickness of the first hydrophobic layer and the thickness of the second hydrophobic layer are different. In certain embodiments, the thickness of the first hydrophobic layer is about 50 nm to about 200 nm, about 60 nm to about 190 nm, about 70 nm to about 180 nm, about 80 nm to about 170 nm, about 90 nm to about 160 nm, about 100 nm to about 150 nm, about 110 nm to about 140 nm, or about 120 nm to about 130 nm. In certain embodiments, the thickness of the first hydrophobic layer is about 100 nm. In certain embodiments, the thickness of the second hydrophobic layer is about 50 nm to about 200 nm, about 60 nm to about 190 nm, about 70 nm to about 180 nm, about 80 nm to about 170 nm, about 90 nm to about 160 nm, about 100 nm to about 150 nm, about 110 nm to about 140 nm, or about 120 nm to about 130 nm. In certain embodiments, the thickness of the second hydrophobic layer is about 100 nm. In certain embodiments, the first hydrophobic layer is formed by polytetrafluoroethene (PTFE), i.e. Teflon AF. In certain embodiments, the second hydrophobic layer is formed by polytetrafluoroethene (PTFE), i.e. Teflon. In certain embodiments, the first and the second hydrophobic layers are polytetrafluoroethene (PTFE), i.e. Teflon, having a thickness of about 100 nm.

The upper layer 200 can comprise at least one top heater 204, and the lower layer 300 can comprise at least one thermal electrode 307 for heating the droplet 600 and sensing a temperature of the droplet 600. The at least one thermal electrode 307 can be provided in a spaced relationship relative to each of the at least one top heater 204, thus defining a space between the each of the at least one thermal electrode 307 and the each of the at least one top heater 204 capable of contacting each of the at least one droplet 600 between the second hydrophobic working surface 203-1 and the first hydrophobic working surface 301-1. In other words, each of the at least one top heater 204 and each of the at least one thermal electrode 307 can form a pair of dual heaters, wherein the center of the top heater 204 and the center of the thermal electrode 307 are positioned approximately along the same line that is perpendicular to the upper layer 200 or the lower layer 300 to achieve maximum heating efficiency. The incorporation of dual heaters into the digital microfluidic device can provide heat from both top and bottom to a droplet comprising PCR mixtures, and hence reduce the temperature differences within the droplet, lower the heating voltage, and shorten the reaction time. In certain embodiments, the microfluidic device 100 further comprises a heat disseminating element on top of the upper layer 200 to expedite the cooling of the droplet. In certain embodiments, the heat disseminating element is a fan.

Figure 2:
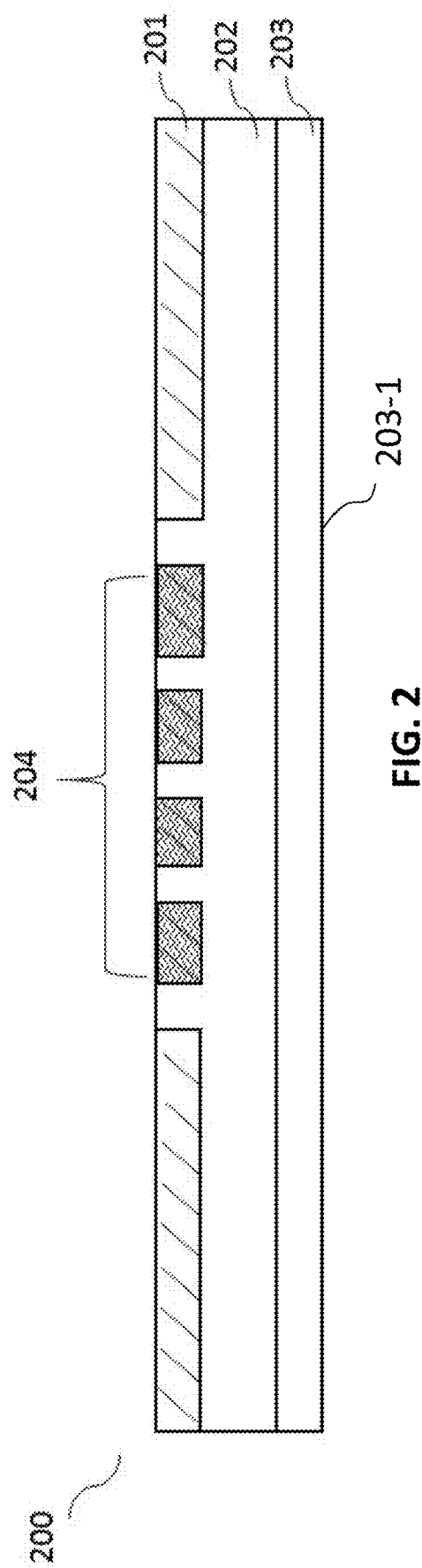
FIG. 2 illustrates a cross-sectional view of an upper layer of the digital microfluidic device according to certain embodiments of the present disclosure.

FIG. 2 illustrates a cross-sectional view of an upper layer 200 of the digital microfluidic device 100 according to certain embodiments of the present disclosure. The upper layer 200 can comprise a second substrate 202, at least one top heater 204 formed by at least one second coating 201 covering an outer side of the second substrate 202, and a second hydrophobic layer 203 formed on an inner side of the second substrate 202 to provide a second hydrophobic working surface 203-1.

In certain embodiments, the second substrate 202 is a glass plate. In certain embodiments, the second substrate 202 has a thickness of about 0.1 mm to about 1.0 mm, about 0.2 mm to about 0.9 mm, about 0.3 mm to about 0.8 mm, about 0.4 mm to about 0.7 mm, or about 0.5 mm to about 0.6 mm. In certain embodiments, the second substrate 202 has a thickness of about 0.4 mm. In certain embodiments, the second coating 201 is an indium tin oxide (ITO) coating. In certain embodiments, the at least one top heater 204 is formed by cutting the ITO-coated glass by a laser cutter.

Figure 3:
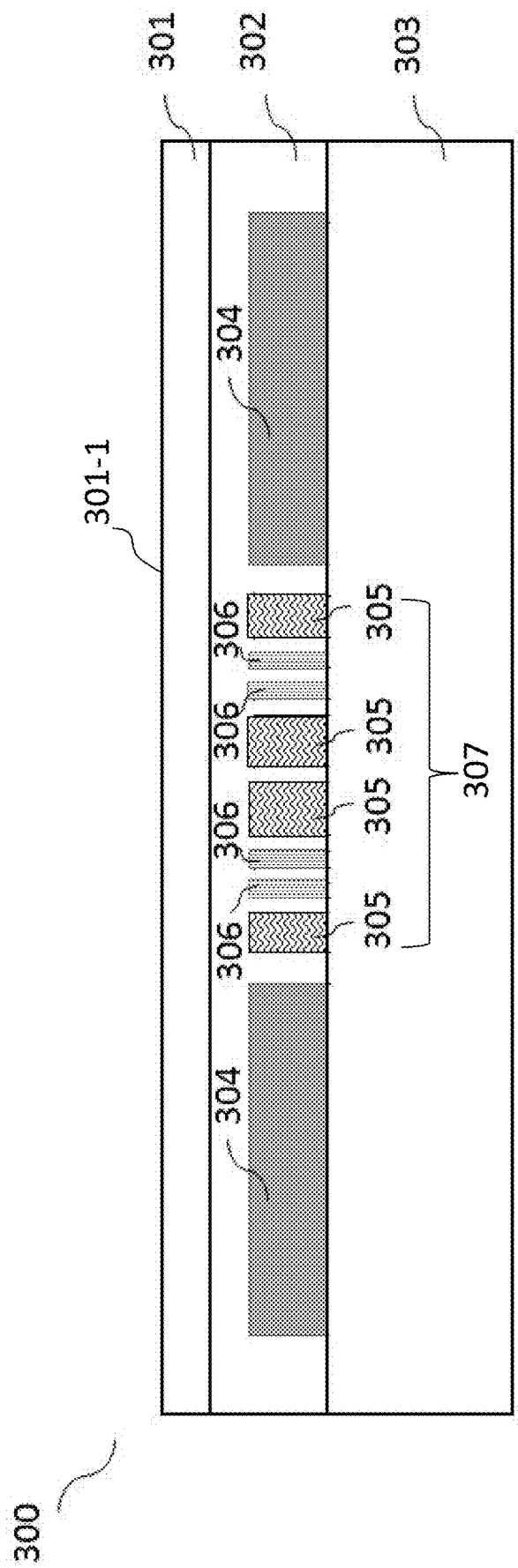
FIG. 3 illustrates a cross-sectional view of a lower layer of the digital microfluidic device according to certain embodiments of the present disclosure.

FIG. 3 illustrates a cross-sectional view of a lower layer 300 of the digital microfluidic device 100 according to certain embodiments of the present disclosure. The lower layer 300 can comprise a first substrate 303, an array of electrodes comprising at least one thermal electrode 307 formed on an inner side of the first substrate 303, at least one first coating 302 covering each of the array of electrodes such that the array of electrodes are electrically insulated from one another, and a first hydrophobic layer 301 formed on the at least one first coating 302 to provide a first hydrophobic working surface 301-1.

In certain embodiments, the first substrate 303 is a glass plate. In certain embodiments, the first substrate 303 has a thickness of about 0.5 mm to about 2.5 mm, about 0.6 mm to about 2.4 mm, about 0.7 mm to about 2.3 mm, about 0.8 mm to about 2.2 mm, about 0.9 mm to about 2.1 mm, about 1.0 mm to about 2.0 mm, about 1.1 mm to about 1.9 mm, about 1.2 mm to about 1.8 mm, about 1.3 mm to about 1.7 mm, about 1.4 mm to about 1.6 mm, or about 1.5 mm. In certain embodiments, the first substrate 303 has a thickness of about 1.5 mm.

In certain embodiments, the first coating 302 is an ultraviolet curable resin as a dielectric layer. The dielectric layer should be 100% solid but soft; it should not peel off easily from the substrate during thermal expansion and contraction in the process of heating and cooling. In certain embodiments, the first coating 302 has a thickness of about 5 µm to about 25 µm, about 6 µm to about 24 µm, about 7 µm to about 23 µm, about 8 µm to about 22 µm, about 9 µm to about 21 µm, about 10 µm to about 20 µm, about 11 µm to about 19 µm, about 12 µm to about 18 µm, about 13 µm to about 17 µm, about 14 µm to about 16 µm, or about 15 µm. In certain embodiments, the first coating 302 has a thickness of about 10 µm. In certain embodiments, the first coating 302 is SU-8 negative photoresist, AZ positive photoresist, polyimide film or the like. In certain embodiments, the first coating 302 is Norland Optical Adhesive 61, which is cured from a clear and colorless liquid photopolymer, and works as a dielectric layer. The Norland Optical Adhesive 61 dielectric layer has advantages over previous dielectric layers used for the digital microfluidic device, such as SU8 photoresist. For example, the SU8 photoresist is prone to being breakdown under a certain time of thermal cycling (e.g. about 3 min), but the Norland Optical Adhesive 61 dielectric layer can stay intact even after a longer time of thermal cycling (e.g. about 6 min). Moreover, the Norland Optical adhesive 61 dielectric layer is softer than the SU-8 dielectric layer and can protect the sensor electrode 306 from being damaged.

Figure 4:
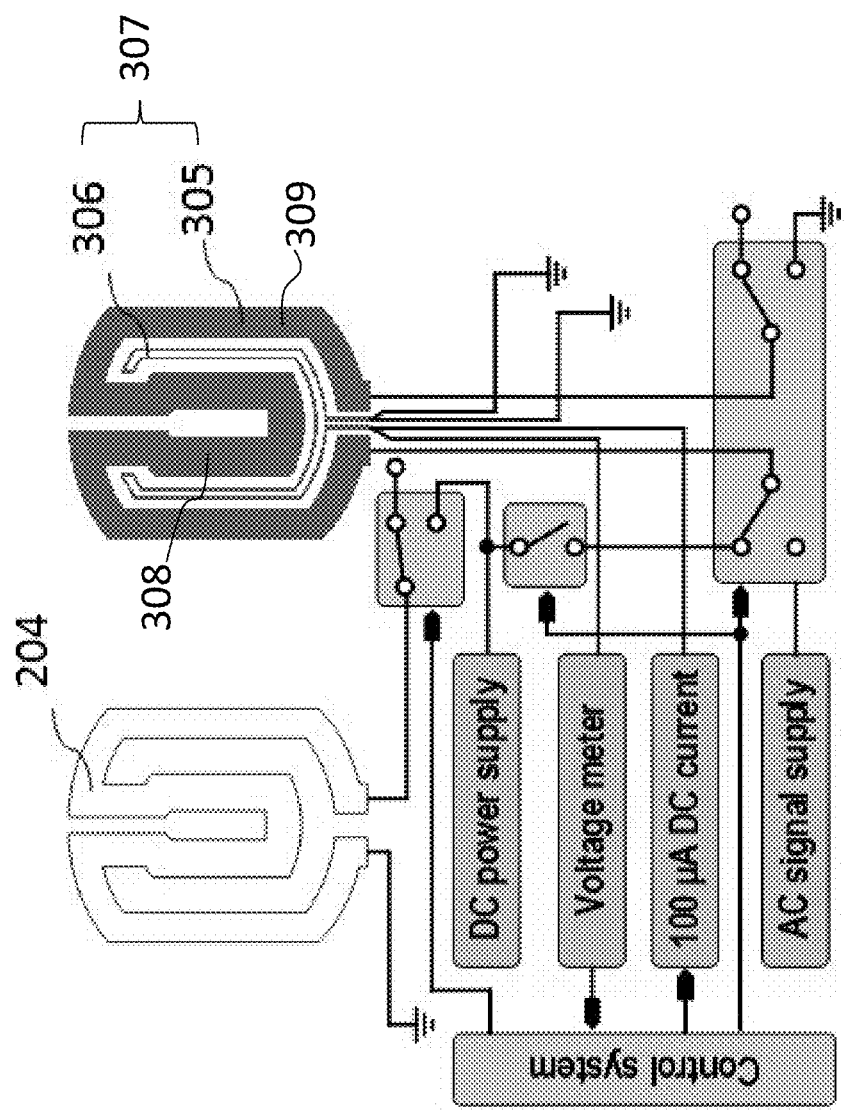
FIG. 4 illustrates the control electronics of the thermal electrode according to certain embodiments of the present disclosure.

In certain embodiments, the thermal electrode 307 comprises at least one heater electrode 305 and at least one sensor electrode 306 all arranged to be co-planar to each other, as shown in FIG. 4. The heater electrode 305 can be serpentine-shaped with an inner ring 308 and an outer ring 309, as shown in FIG. 4. In certain embodiments, the width of the inner ring 308 is larger than the width of the outer ring 309, in order to prevent the central temperature from being too high.

In certain embodiments, the inner ring 308 has a width of about 300 µm to about 400 µm, about 310 µm to about 390 µm, about 320 µm to about 380 µm, about 330 µm to about 370 µm, about 340 µm to about 360 µm, or about 350 µm. In certain embodiments, the inner ring 308 has a width of about 349 µm. In certain embodiments, the outer ring 309 has a width of about 200 µm to about 300 µm, about 210 µm to about 290 µm, about 220 µm to about 280 µm, about 230 µm to about 270 µm, about 240 µm to about 260 µm, or about 250 µm. In certain embodiments, the outer ring 309 has a width of about 279 µm. In certain embodiments, the inner ring 308 has a width of about 349 µm, and the outer ring 309 has a width of about 279 µm.

The heater electrode 305 and the sensor electrode 306 are parallel to each other and have a gap of at least about 100 µm in order to prevent the fine sensor electrode to be damaged.

In certain embodiments, the array of electrodes including the thermal electrode 307 are made from chromium (Cr). In certain embodiments, the array of electrodes are an array of square Cr electrodes 304.

As shown in FIG. 4, the at least one heater electrode 305 and the at least one top heater 204 can be connected to an adjustable direct current (DC) power supply to form a first mode for providing heat to the at least one droplet 600 from both the top and the bottom thereof. The at least one heater electrode 204 can also be connected to an alternating current (AC) power supply to form a second mode for transporting the at least one droplet 600 from the inlet to the at least one thermal electrode 307 or the dual heaters 204/305. In certain embodiments, the at least one sensor electrode 306 is connected to a direct current (DC) power supply and a voltage indicator to form a third mode for recording temperatures, which can be converted from the measured voltages, of the at least one droplet 600. In certain embodiments, the voltage indicator is a multimeter or an analog-to-digital (ADC) converter.

The adjustable DC power supply and the AC power supply can be in electrical communication with and downstream a control system, which is in electrical communication with and downstream the voltage indicator. As such, the voltage (temperature) information detected by the voltage indicator can be transmitted to the control system, which in turn can modulate the adjustable DC power supply. For example, if the voltage (temperature) detected by the voltage indicator is higher than a first preset threshold, the control system can disconnect the adjustable DC power supply from the dual heaters, so as to switch the device to a cooling status; if the voltage (temperature) detected by the voltage indicator is lower than a second preset threshold, the control system can re-connect the adjustable DC power supply to the dual heaters, thus switching the device to a heating status.

Figure 5:
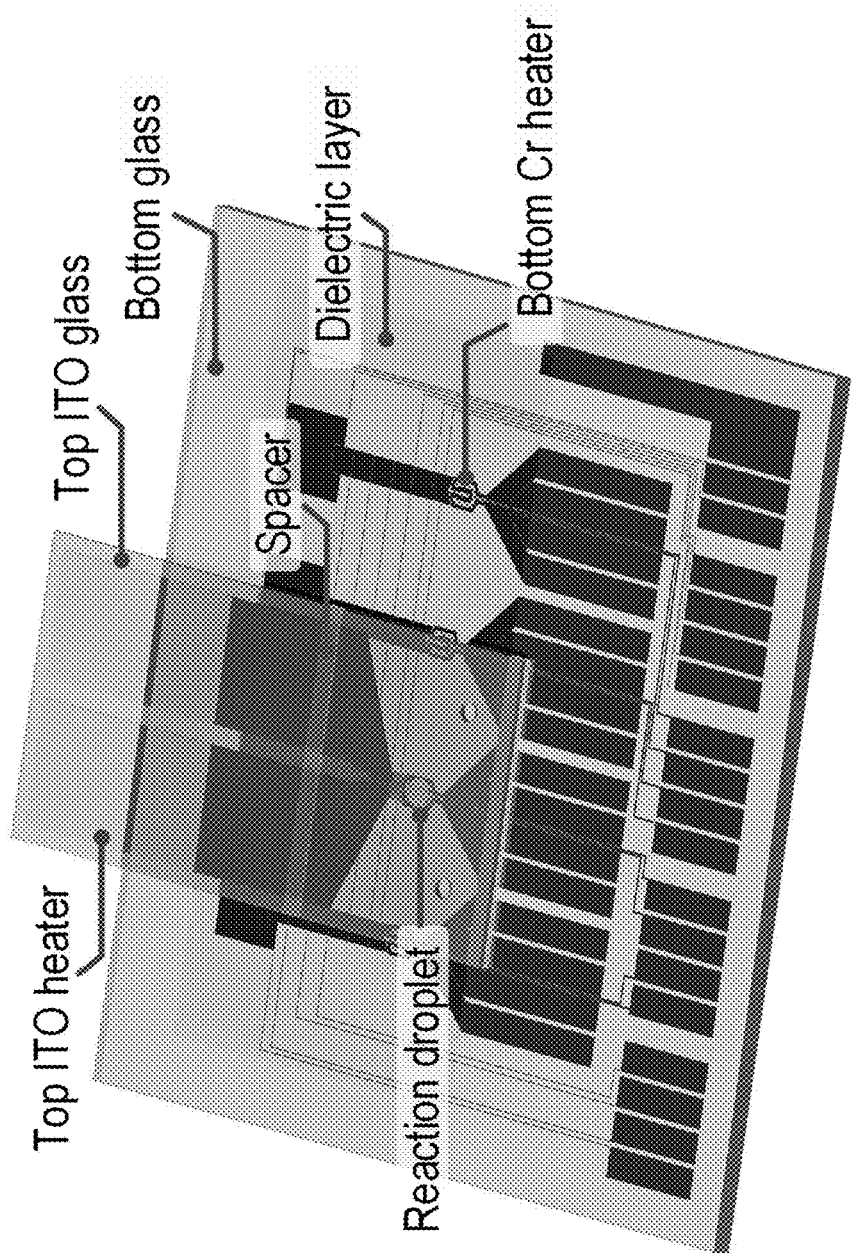
FIG. 5 illustrates the schematic of the digital microfluidic device according to certain embodiments of the present disclosure.

In certain embodiment, the 3D view of the digital microfluidic device is shown in FIG. 5.

Using the Digital Microfluidic Device for Conducting Polymerase Chain Reaction

Figure 6:
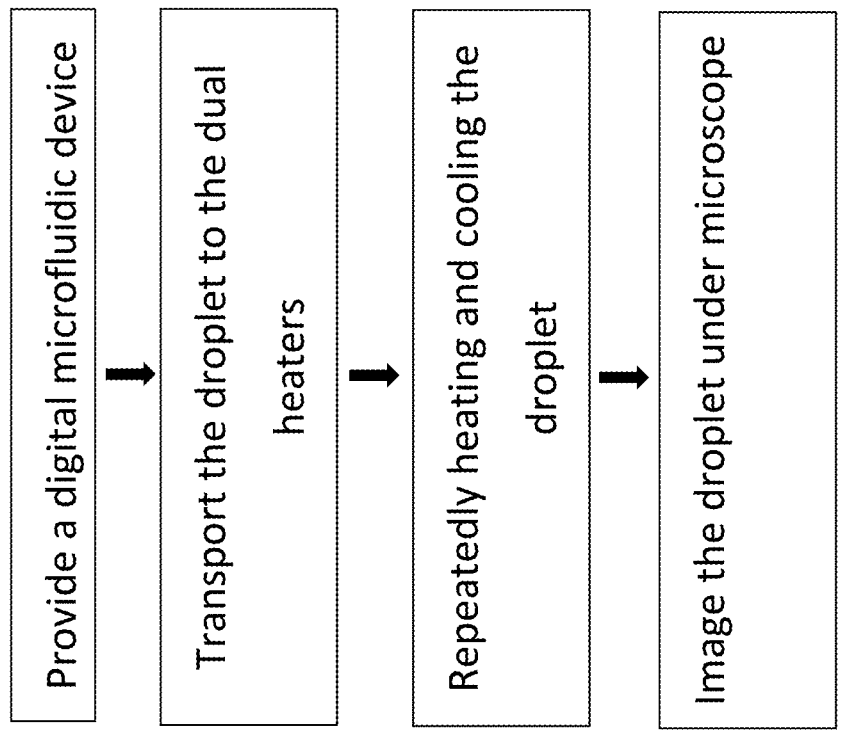
FIG. 6 illustrates the work flow of the method of conducting PCR using the digital microfluidic device according to certain embodiments of the present disclosure.

A complete method for quick polymerase chain reaction (PCR) will now be described with reference to the digital microfluidic device of the present disclosure, as shown in FIG. 6.

Preparation of Loading Fluid

In certain embodiments, the loading fluid is a PCR mixture comprising a target DNA sequence, primers, one DNA probe, and one or more buffer solutions. In certain embodiments, the DNA probe is a Molecular Beacon probe.

Assembling the Digital Microfluidic System

In certain embodiments, the digital microfluidic system comprises a device holder with a digital microfluidic device, control electronics, customized control software, and a fluorescence microscope. The digital microfluidic device can be inserted into a 3D-printed device holder, which can be embedded with a printed circuit board (PCB) for connecting the electrodes of the digital microfluidic device to the control electronics. The customized control software can collect the temperature data and position information of the droplet comprising the PCR mixture via the control electronics and carry out the droplet manipulation (e.g. transportation) or thermal-modulation (e.g. heating and cooling) protocols. The device holder with a plug-in digital microfluidic device can be put on the stage of a fluorescence microscope during the experiments, e.g. polymerase chain reaction (PCR). The control electronics can support droplet manipulation and thermal modulation. The thermal modulation can be based on a software intensive proportional-integral-derivative (PID) controller with temperature feedback. The thermal electrode 307 can support two functions depending on its power supply: it can be connected to a DC source (12-30 V) to function as a heater together with the top heater 204, and to an AC source (100-150 $V_{rms}$ 1 kHz, square wave) to function as a normal electrode for droplet manipulation (e.g. transportation).

Transport the Droplet to the Dual Heaters

In certain embodiments, the microfluidic system comprises an intelligent closed-loop control system to monitor the droplet coverage on an electrode by measuring the capacitance between the electrode and the ground in real time. During the transportation of the droplet 600 formed from a loading fluid, the first electrode of the array of electrodes keeps sensing for the loading fluid. Once the coverage of the loading fluid on the first electrode reached a pre-set threshold value (20% of electrode area), the sample loading procedure can be activated. The coverage on the first electrode and the second electrode can be tracked in real time. As soon as 95% of the first electrode is covered, the second electrode can be charged. When 95% of the second electrode is covered, the loading fluid starts to be extracted through the inlet by discharging the first electrode while continuing to charge the second electrode. During extraction, the fluid coverage on the first electrode can be monitored in real time. Once the coverage goes down to 20%, the second electrode can be discharged in 0.5 seconds while the loading fluid is drawing. As a result, a droplet 600 can be generated with high reproducibility and leave on the second electrode. This automatic transportation of the loading fluid can significantly reduce the sample loading time to coordinate with the ultrafast PCR.

Calibrating the Thermal Electrode

As shown in FIG. 4, the thermal electrode 307 can have three modes: a heating mode (a first mode), a transporting mode (a second mode), and a sensing mode (a third mode). The thermal electrode 307 can be switched to a heating mode by connecting the dual heaters (both the top heater 204 and the bottom heater electrode 305) in parallel to the same DC source (12-30V). The thermal electrode 307 can be switched to a transporting mode by connecting the heater electrode 305 to an AC source (100-150 $V_{rms}$, 1 kHz, square wave). The thermal electrode 307 can be switched to a sensing mode by connecting the sensor electrode 306 to a 100 μA DC current. The voltage sensed by the sensor electrode 306 (sensing voltage) can be measured a voltage indicator. In certain embodiments, the voltage indicator is a multimeter or an analog-to-digital (ADC) converter.

Before the on-chip PCR reaction, the sensor electrode 306 can be calibrated for its temperature and resistance using a 4-wire resistance measurement, as shown in FIG. 4. The 4-wire measurement can make sure that the relationship between temperature and resistance is not interfered by the resistance of the long thin wires.

Figure 7B:
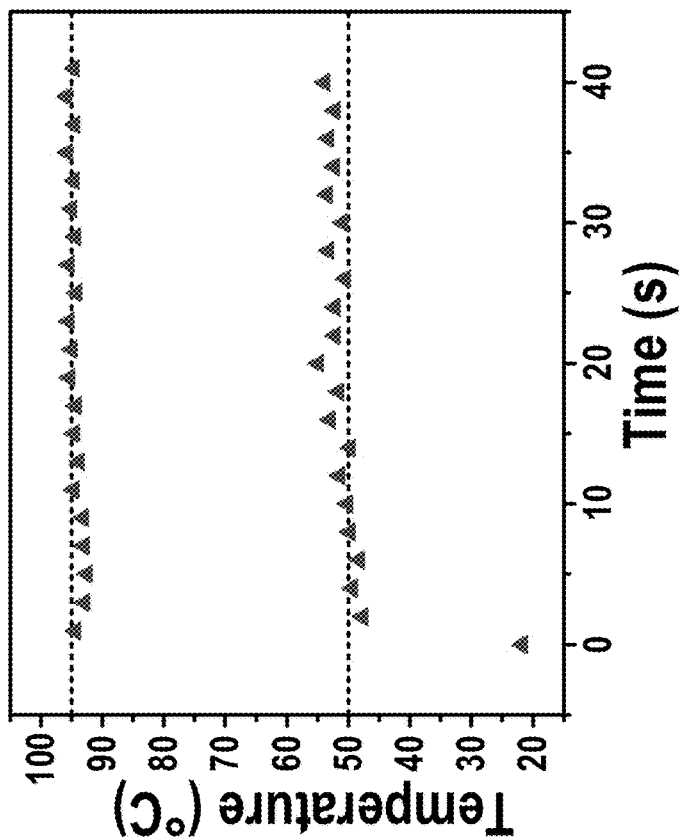
FIG. 7B shows the temperature of the thermal cycles by sloppy control according to certain embodiments of the present disclosure.
Figure 7A:
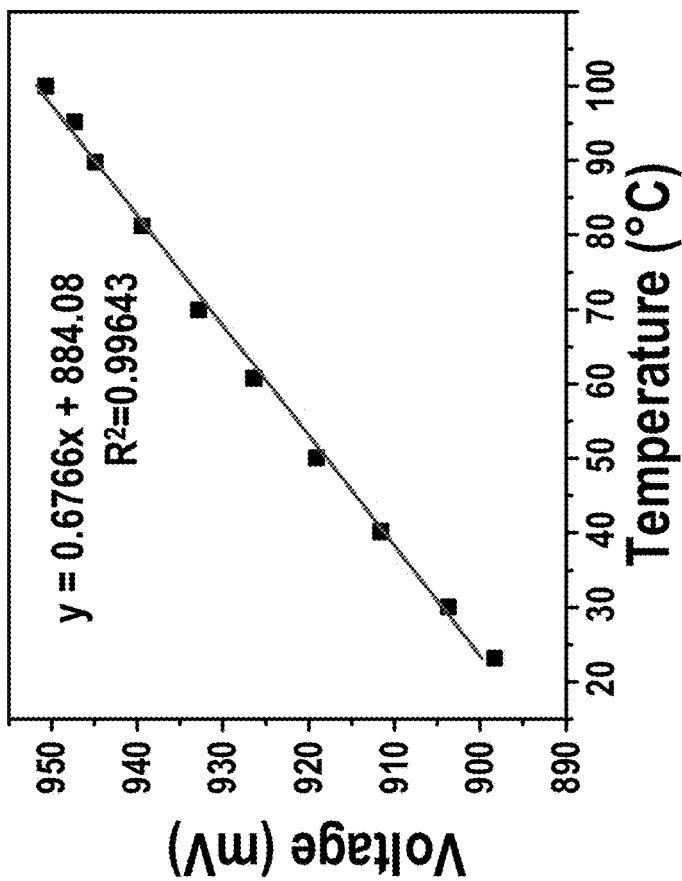
FIG. 7A shows the linear relationship between the sensing voltage and temperature of the sensor electrode according to certain embodiments of the present disclosure.

FIG. 7A shows that the sensing voltage and the temperature of the sensor are in linear relationship.

Repeatedly Heating and Cooling the Droplet

After the digital microfluidic device 100 is loaded with droplets comprising e.g. PCR mixtures at the dual heaters 204/305, a sensing voltage ($V_{sense}$) at room temperature can be recorded and the $V_{sense}$ at 50° C. and 95° C. can be calculated according to the linear relationship shown in FIG. 7A. After this, an adjustable DC power can be supplied to the thermal electrode 307 to obtain three lengths of time through heating and cooling, as shown in Table 1.

TABLE 1

Thermal profile of on-chip PCR.

| Status | Time | Temperature | |
|---|---|---|---|
| Heater on | t1 | RT-95° C. | |
| Heater off | t2 | 95° C.-50° C. | |
| Heater on | t3 | 50° C.-95° C. | 2 thermal |
| Heater off | t2 | 95° C.-50° C. | cycles |
| Heater on | t3 − t s | Cycle | |
| Heater off | t2 + t s | correction | |

After that, the PCR reaction can start with a heating time (t3) and a cooling time (t2). Then, to prevent the heat accumulation, this step further comprises a thermal cycle's correction by reducing the heating time (t3) by 0.1-0.5 s and increasing the cooling time (t2) by 0.1-0.5 s. The heating time (t3) is the time for increasing temperature from about 50° C. to about 95° C., and the cooling time (t2) is the time for reducing temperature from about 95° C. to about 50° C. Then the PCR runs for 50-200 cycles with each cycle containing 4 steps: t3 (a first length of time), t2 (a second length of time), t3 reduced by 0.1-0.5 s (a third length of time) and t2 increased by 0.1-0.5 s (a fourth length of time) for 50-200 cycles. The upper and lower temperature can be stabilized at 95° C. and 50° C. respectively under this thermal profile, as shown in FIG. 7B.

In certain embodiments, the t1, t2, and t3 of the digital microfluidic device according to certain embodiments of the present disclosure are 4.5 s, 3 s, and 2.5 s respectively, and the total time spent for each PCR cycle is 5.7 s. The ramping rate and cooling rate can be 11.6° C./s and 8.5° C./s respectively.

Imaging the Droplet Under Fluorescence Microscope

Figure 8A:
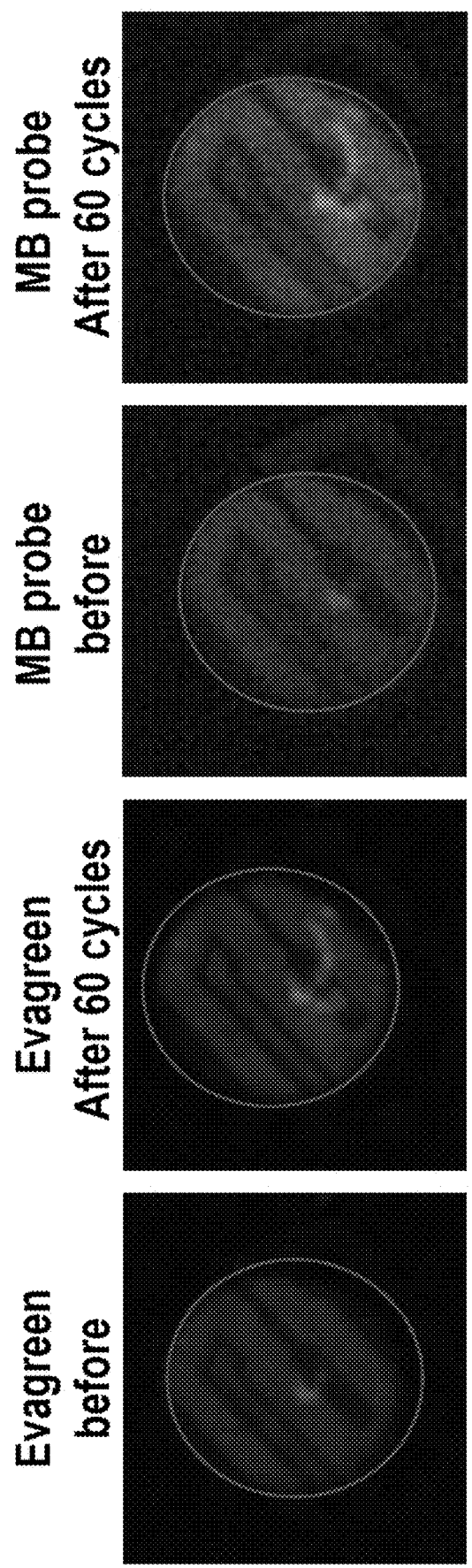
FIG. 8A shows the microscopic images of the droplet at the thermal electrode according to certain embodiments of the present disclosure.
Figure 8B:
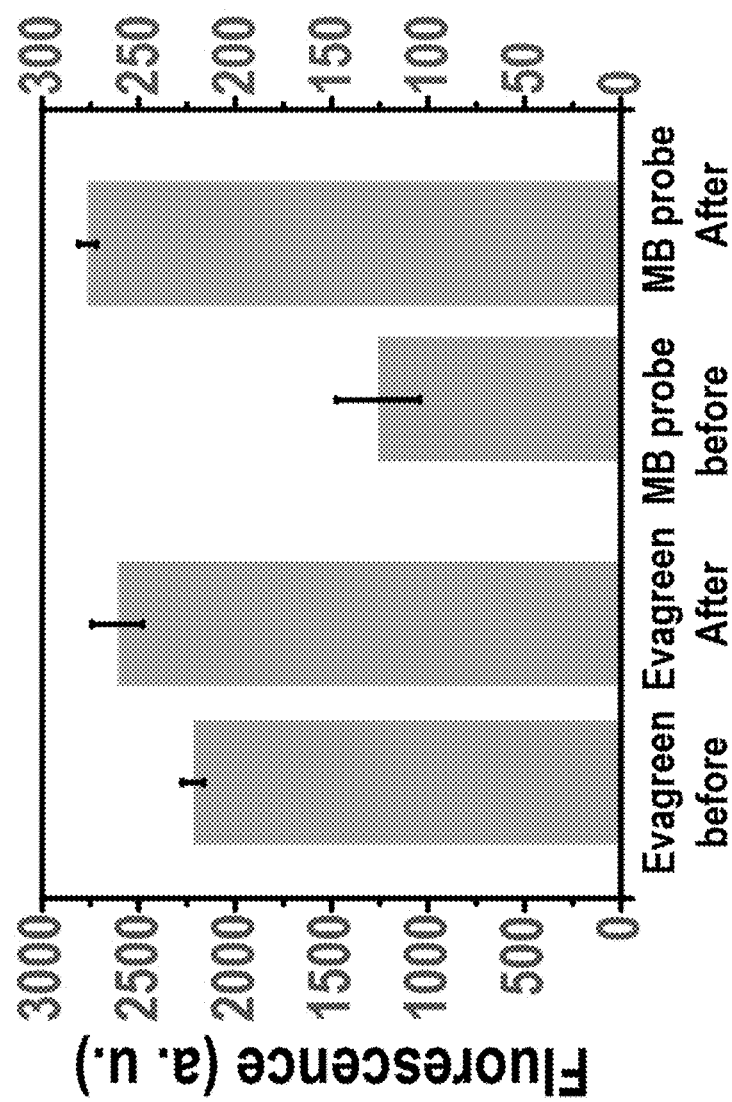
FIG. 8B shows a bar graph of the fluorescent intensity of the microscopic images according to certain embodiments of the present disclosure.
Figure 8C:
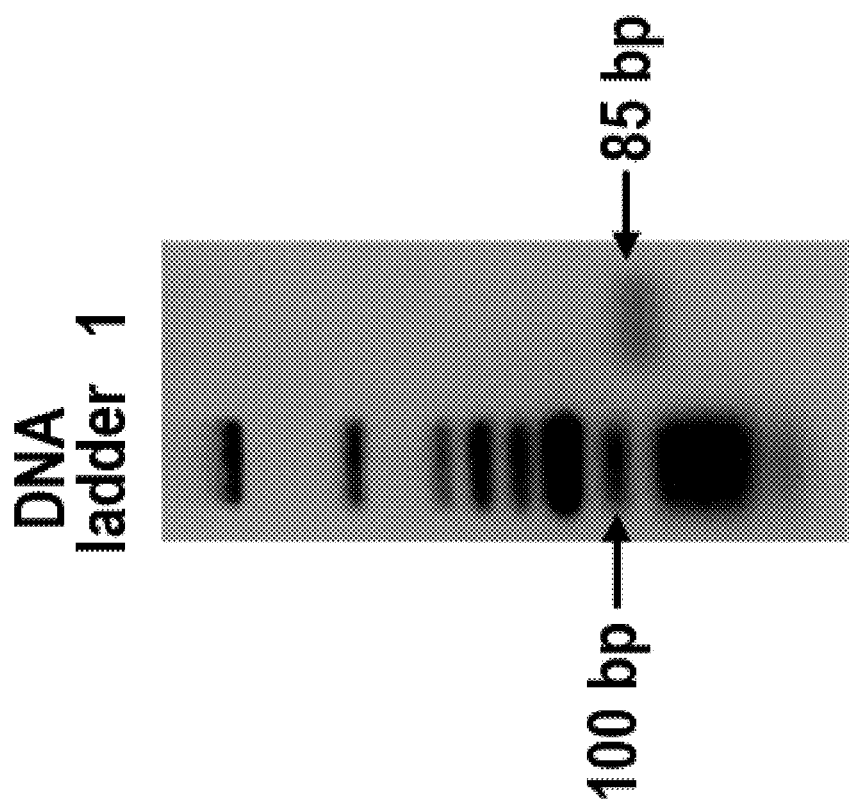
FIG. 8C shows the Agarose gel electrophoresis result of the on-chip PCR product according to certain embodiments of the present disclosure.

In certain embodiments, the digital microfluidic device with droplets containing PCR mixtures is placed under a microscope system for acquisition of images of the droplet during PCR cycles. FIG. 8A and FIG. 8B show that the PCR reaction conducted in the digital microfluidic device according to certain embodiments of the present disclosure can successfully amplify detectable products as early as 60 cycles (342 s) in less than 6 min using fluorescence microscope. FIG. 8C shows that the detected PCR product can be further confirmed by agarose gel electrophoresis.

Example 1: Thermal Electrode Design

In this example, the thermal electrode is made from chromium, and is flat and oval-shaped. The thermal electrode comprises two components: a serpentine heater electrode and a fork-shaped sensor electrode parallelizing with each other. The heater electrode is designed and optimized computationally through Comsol. The width of the inner ring of the heater electrode (349 μm) is wider than the outer ring of the heater electrode (279 μm) in order to prevent the central temperature being too high. The gaps between the heater electrode and the sensor electrode are over 100 μm to prevent the fine sensor electrode damage.

Example 2: Fabrication of the Digital Microfluidic Device

The digital microfluidic device/chip is a sealed disposable chip. A bottom glass plate (1.5 mm) is patterned with an array of square chromium (Cr) electrodes and the thermal electrodes. A 10 μm-thick clear, colorless, liquid photopolymer—Norland Optical Adhesive 61 was spin-coated and UV cured on the bottom plate as the dielectric layer. Then, 100 nm Teflon was coated on the bottom plate to create a hydrophobic surface for smooth droplet transportation. A 0.4 mm ITO glass was used as the top plate. The top heater pattern was cut by a laser cutter. Teflon was coated on the opposite side of the ITO glass and the Teflon side of the ITO glass faced downward. Finally, the bottom and top plates were separated by a 200 μm oil-proof double adhesive and sealed with UV glue. Thus an enclosed reaction chamber was formed to prevent potential contamination during and after the reaction. Hexadecane oil and PCR reaction mixture were loaded through the inlet holes (1.2 mm diameter) drilled using a laser cutter on the top plate.

Example 3: PCR Testing System

A human HEXA gene G269 allele responsible for the Tay-Sachs disease was used as a model system. To enhance the PCR specificity, we adopted linear-after-the-exponential PCR (LATE-PCR) which synthesizes single-stranded DNA in an efficient way combined with a low-melting-temperature ($T_m$) Molecular Beacon DNA probe as a specific indicator for true-positive results. The primers and probe sequence were listed below:

Limiting primer:
5'-GCCCTTACATAGTCTAACAGTACATA-3'

Excess primer:
5'-GGGAATTTAGATAGGAAGAACTC-3'

Molecular Beacon probe:
5'-Quasar570-CGTGCTCCATTGTCCAAACACG-BHQ2-3'

The target sequence was 85 bp. The PCR reaction mix in this work consisted of 2× SsoFast EvaGreen supermix, 200 nM limiting primer, 1 µM excess primer, 500 nM Molecular Beacon probe, 1×additive reagent, and ddH$_2$O. Plasmids target was diluted in tris-EDTA (TE) buffer to a final concentration of $10^6$ copies. A no-template control (NTC) sample with a TE buffer, rather than DNA, was included in each run as a negative control for detecting contamination amplification in the reaction.

The off-chip real-time PCR was run in 10 µl per reaction in a conventional PCR machine (Bio-Rad CFX96™) as a control of the on-chip PCR. The thermal profile was adapted to mimic the fast PCR condition on chip. 60 thermal cycles were run repeating 95° C. for 1 s and 50° C. for 1 s (signal recorded took ~12 s) for off-chip PCR.

CONCLUSIONS

In summary, this DMF platform with on-chip dual-heater micro-thermal cycler by sloppy temperature control has successfully run a fast PCR within 6 minutes. The LATE-PCR with Molecular Beacon DNA probe wipes out false-positive as well as providing possibility for mutation detection. The entire platform is open for further integration with sample preparation and fluorescence detection towards a total-micro-analysis system.

Although the invention has been described in terms of certain embodiments, other embodiments apparent to those of ordinary skill in the art are also within the scope of this invention. Accordingly, the scope of the invention is intended to be defined only by the claims which follow.

The invention claimed is:

1. A digital microfluidic device (100) for conducting quick polymerase chain reaction in at least one droplet (600) generated from a loading, fluid, the device (100) comprising an upper layer (200), a lower layer (300), a lateral wall (400) positioned between the upper layer (200) and the lower layer (300) to form a chamber, an inlet for receiving the loading fluid and providing the loading fluid to the chamber, and an outlet for releasing trapped air and extra loading fluid during a loading process, wherein:
  the lower layer (300) comprises:
    a first substrate (303);
    an array of electrodes comprising at least one thermal electrode (307) formed on an inner side of the first substrate (303), an individual thermal electrode comprising a heater electrode (305) and a sensor electrode (306);

at least one first coating (302) covering each electrode of the array of electrodes such that all electrodes of the array of electrodes are electrically insulated from one another; and a first hydrophobic layer (301) formed on the at least one first coating (302) to provide a first hydrophobic working surface (301-1), the heater electrode (305) being serpentine-shaped having an inner ring (308) and an outer ring (309); and the sensor electrode (306) being fork-shaped and positioned between the inner ring (308) and the outer ring (309) of the heater electrode (305), the upper layer (200) comprises:

a second substrate (202), at least one top heater (204) formed by at least one second coating (201) covering an outer side of the second substrate (202), and a second hydrophobic layer (203) being formed on an inner side of the second substrate (202) to provide a second hydrophobic working surface (203-1), wherein each of the at least one thermal electrode (307) is positioned right below a corresponding top heater (204) to create a space in the chamber between each of the at least one thermal electrode (307) and the corresponding top heater (204), the top heater (204) and the corresponding thermal electrode (307) being capable of contacting a corresponding droplet (600) located between the second hydrophobic working surface (203-1) and the first hydrophobic working surface (301-1) such that the corresponding droplet receives heat from both the upper and lower layers.

2. The digital microfluidic device (100) of claim 1, wherein the at least one second coating (201) is an indium tin oxide coating.

3. The digital microfluidic device (100) of claim 1, wherein the at least one first coating (302) is an ultraviolet curable resin.

4. The digital microfluidic device (100) of claim 1, wherein the at least one first coating (302) is a dielectric layer.

5. The digital microfluidic device (100) of claim 1, wherein the inner ring (308) is wider than the outer ring (309).

6. The digital microfluidic device (100) of claim 5, wherein the inner ring (308) has a width of about 300 μm to about 400 μm, and the outer ring (309) has a width of about 200 μm to about 300 μm.

7. The digital microfluidic device (100) of claim 6, wherein the inner ring (308) has a width of about 349 μm, and the outer ring (309) has a width of about 279 μm.

8. The digital microfluidic device (100) of claim 1, wherein the at least one heater electrode (305) and the at least one sensor electrode (306) have a distance of larger than about 100 μm.

9. The digital microfluidic device (100) of claim 1, wherein the at least one heater electrode (305) and the at least one top heater (204) can be connected to an adjustable direct current (DC) power supply to form a first mode for providing heat to the at least one droplet (600).

10. The digital microfluidic device (100) of claim 1, wherein the at least one heater electrode (305) can be connected to an alternating current (AC) power supply to form a second mode fir transporting the at least one droplet (600) from the inlet to the at least one thermal electrode (307).

11. The digital microfluidic device (100) of claim 1, wherein the at least one sensor electrode (306) can be connected to a direct current (DC) power supply and a voltage indicator to form a third mode for recording temperature of the at least one droplet (600).

12. A method for conducting quick polymerase chain reaction, comprising steps of:

a) providing the digital microfluidic device (100) of claim 1;

b) transporting at least one droplet (600) generated from a loading fluid to the at least one thermal electrode (307) of the digital microfluidic device (100) of claim 1;

repeatedly heating the at least one droplet (600) for a first length of time and cooling the at least one droplet (600) for a second length of time followed by heating the at least one droplet (600) for a third length of time and cooling the at least one droplet (600) for a fourth length of time; and d) imaging the at least one droplet (600).

13. The method of claim 12, further comprising between the step a) and the step b) a step e): calibrating the at least one sensor electrode (306) to obtain a linear relationship between temperature sensed by the at least one sensor electrode (306) and voltage measured by a voltage indicator connected to the at least one sensor electrode (306).

14. The method of claim 12, wherein the loading fluid comprises at least one primer, at least one DNA indicator, and at least one target DNA sequence.

15. The method of claim 12, wherein the first length of time is time for increasing temperature from about 50° C. to about 95° C., and the second length of time is time for reducing temperature from about 95° C. to about 50° C.

16. The method of claim 12, wherein the third length of time is obtained by reducing the first length of time by 0.1-0.5 seconds, and the fourth length of time is obtained by increasing the second length of time by 0.1-0.5 seconds.

* * * * *

SEQUENCE LISTING

<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Limiting primer, synthesized in lab

<400> SEQUENCE: 1
gcccttacat agtctaacag tacata                                        26

<210> SEQ ID NO 2
<211> LENGTH: 23
<212> TYPE: DNA
<213> ORGANISM: Artificial Sequence
<220> FEATURE:
<223> OTHER INFORMATION: Excess primer, synthesized in lab

<400> SEQUENCE: 2
gggaatttag ataggaagaa ctc                                           23

<210> SEQ ID NO 3
<211> LENGTH: 22
<212> TYPE: DNA
<213> ORGANISM: Artificial Sequence
<220> FEATURE:
<223> OTHER INFORMATION: Molecular Beacon probe, Synthesized in lab

<400> SEQUENCE: 3
cgtgctccat tgtccaaaca cg                                            22